(12) United States Patent
Chang

(10) Patent No.: US 11,602,283 B2
(45) Date of Patent: Mar. 14, 2023

(54) PATIENT MONITORING SYSTEM FOR CONGESTIVE HEART FAILURE DETECTION AND RELATED METHODS

(71) Applicant: Khai S. Chang, Mount Dora, FL (US)

(72) Inventor: Khai S. Chang, Mount Dora, FL (US)

( * ) Notice: Subject to any disclaimer, the term of this patent is extended or adjusted under 35 U.S.C. 154(b) by 348 days.

(21) Appl. No.: 16/932,081

(22) Filed: Jul. 17, 2020

(65) Prior Publication Data

US 2022/0015666 A1 Jan. 20, 2022

(51) Int. Cl.
*A61B 5/085* (2006.01)
*A61B 5/00* (2006.01)
*A61B 5/1455* (2006.01)
*A61B 5/103* (2006.01)

(52) U.S. Cl.
CPC .............. *A61B 5/085* (2013.01); *A61B 5/002* (2013.01); *A61B 5/0024* (2013.01); *A61B 5/103* (2013.01); *A61B 5/1455* (2013.01); *A61B 5/7275* (2013.01); *A61B 2560/04* (2013.01); *A61B 2562/0247* (2013.01)

(58) Field of Classification Search
CPC ....... A61B 5/6892; A61B 5/085; A61B 5/002; A61B 5/0024; A61B 5/103; A61B 5/1455; A61B 5/7275; A61B 2562/0247; A61B 5/0004; A61B 5/02416; A61B 5/0537; A61B 2560/04
See application file for complete search history.

(56) References Cited

U.S. PATENT DOCUMENTS

| | | |
|---|---|---|
| 7,445,605 B2 | 11/2008 | Overall et al. |
| 7,539,533 B2 | 5/2009 | Tran |
| 8,108,036 B2 | 1/2012 | Tran |
| 8,112,148 B2 | 2/2012 | Giftakis et al. |
| 8,449,471 B2 | 5/2013 | Tran |
| 8,684,900 B2 | 4/2014 | Tran |
| 8,684,922 B2 | 4/2014 | Tran |
| 9,907,473 B2 | 3/2018 | Tran |
| 10,271,791 B2 | 4/2019 | Donnelly et al. |
| 2017/0188956 A1 | 7/2017 | Banet et al. |
| 2018/0280646 A1 | 10/2018 | Freeman et al. |

OTHER PUBLICATIONS

Chen et al. "An Intelligent Telecardiology System Using a Wearable and Wireless ECG to Detect Atrial Fibrillation" IEEE Transactions on Information Technology in Biomedicine, vol. 14, No. 3, May 2010; pp. 8.

(Continued)

*Primary Examiner* — Eric F Winakur
*Assistant Examiner* — Abid A Mustansir
(74) *Attorney, Agent, or Firm* — Allen, Dyer, Doppelt + Gilchrist, P.A. Attorneys at Law

(57) ABSTRACT

A patient monitoring system is for a patient, and may include a base and a frame extending upwardly. The patient monitoring system may include a weight sensor carried by the base, a pair of handrails carried by the frame to be grasped by the patient, and a pair of impedance sensors to be attached to the patient while the patient is on the weight sensor. The patient monitoring system may have a controller coupled to the pair of impedance sensors and the weight sensor and configured to sense a lung impedance of the patient, sense a weight of the patient, and determine whether the patient is experiencing CHF based upon the lung impedance and the weight of the patient.

23 Claims, 7 Drawing Sheets

(56) References Cited

OTHER PUBLICATIONS

Maisel, "B-Type Natriuretic Peptide Levels: A Potential Novel "White Count" for Congestive Heart Failure", Journal of Cardiac Failure, vol. 7, No. 2, Jun. 2001, pp. 183-193.
Dovancescu et al., Detecting Heart Failure Decompensation by Measuring Transthoracic Bioimpedance in the Outpatient Setting: Rationale and Design of the SENTINEL-HF Study, JMIR Research Protocols, Oct. 2015, pp. 1-16.

PATIENT MONITORING SYSTEM FOR CONGESTIVE HEART FAILURE DETECTION AND RELATED METHODS

TECHNICAL FIELD

The present disclosure relates to the field of medical devices, and, more particularly, to patient monitoring system and related methods.

BACKGROUND

As reported by the Centers for Disease Control (CDC), in the United States, 117 million people have chronic health conditions. Patient monitoring systems provide their users and healthcare providers the ability to monitor patients remotely in the event of complications. In particular, for patients with cardiac issues, it may be desirable for healthcare providers to monitor patients on a daily basis.

For instance, patients who have experienced coronary artery disease, including a previous myocardial infarction (heart attack), high blood pressure, and atrial fibrillation, valvular heart disease may be at risk for congestive heart failure (CHF). CHF occurs when the patient's heart fails to pump blood effectively. Because of this, there is a desire to monitor these patients regularly for signs of CHF. One of the commons signs of CHF is rapid weight gain from fluid retention. Hence, for patients at risk for CHF, some healthcare providers ask the patients to record weight on a daily basis.

SUMMARY

Generally, a patient monitoring system for a patient may include a base and a frame extending upwardly therefrom. The patient monitoring system may comprise a weight sensor carried by the base, a pair of handrails carried by the frame to be grasped by the patient, and at least one pair of impedance sensors to be attached to the patient while the patient is on the weight sensor. The patient monitoring system may comprise a controller coupled to the at least one pair of impedance sensors and the weight sensor and configured to sense a lung impedance of the patient, sense a weight of the patient, and determine whether the patient is experiencing CHF based upon the lung impedance and the weight of the patient.

Additionally, the patient monitoring system may further comprise a pair of electrodes respectively carried by the pair of handrails and coupled to the controller. The patient monitoring system may further comprise a pulse oximetry sensor coupled to the controller.

For example, the lung impedance may be between an anterior chest position of the patient, and a posterior back position of the patient, or between a first lateral chest position of the patient, and a second lateral chest position opposite the first lateral chest position of the patient. In some embodiments, the patient monitoring system may further comprise a wireless transceiver coupled to the controller and configured to transmit the lung impedance of the patient and the weight of the patient to a server.

More specifically, the controller may be configured to determine whether the patient is experiencing the CHF based upon the lung impedance being less than an impedance threshold value. The controller may be configured to determine whether the patient is experiencing the CHF based upon the weight of the patient being greater than a weight threshold value. The controller is configured to determine whether the patient is experiencing the CHF based upon a beta natriuretic peptide (BNP) value for the patient being greater than a BNP threshold value. Each impedance sensor comprises an electrode, and a wireless transmitter coupled thereto and configured to communicate with the controller.

Another aspect is directed to a patient monitoring system for a patient. The patient monitoring system may also include a server, and a patient monitoring device in communication with the server. The patient monitoring device may include a base and a frame extending upwardly therefrom, a weight sensor carried by the base, a pair of handrails carried by the frame to be grasped by the patient, and at least one pair of impedance sensors to be attached to the patient while the patient is on the weight sensor. The patient monitoring device may comprise a pair of electrodes respectively carried by the pair of handrails, and a controller coupled to the at least one pair of impedance sensors, the weight sensor, and the pair of electrodes. The controller may be configured to sense a lung impedance of the patient, sense a weight of the patient, and determine whether the patient is experiencing CHF based upon the lung impedance, and the weight of the patient. The patient monitoring device may also include a wireless transceiver coupled to the controller and configured to transmit the lung impedance of the patient, and the weight of the patient.

Yet another aspect is directed to a method of making a patient monitoring system for a patient. The method may also include mounting a weight sensor on a base with a frame extending upwardly therefrom, and mounting a pair of handrails on the frame to be grasped by the patient. The method may comprise providing at least one pair of impedance sensors to be attached to the patient while the patient is on the weight sensor, and coupling a controller to the at least one pair of impedance sensors and the weight sensor and configured to sense a lung impedance of the patient, sense a weight of the patient, and determine whether the patient is experiencing CHF based upon the lung impedance and the weight of the patient.

DETAILED DESCRIPTION

Figure 1:
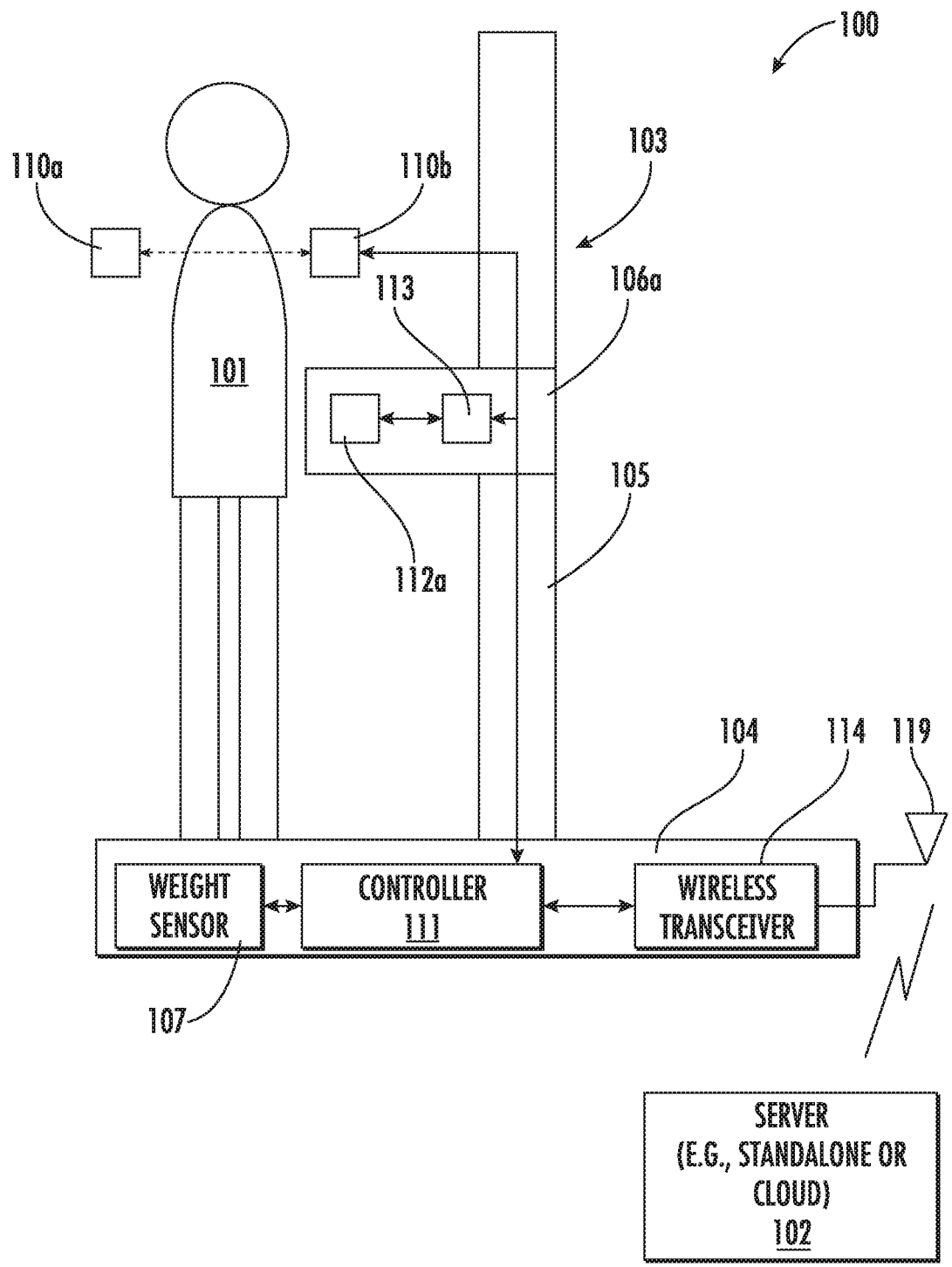
FIG. 1 is a schematic diagram of a first example embodiment of a patient monitoring system, according to the present disclosure.

The present disclosure will now be described more fully hereinafter with reference to the accompanying drawings, in which several embodiments of the invention are shown. This present disclosure may, however, be embodied in many different forms and should not be construed as limited to the embodiments set forth herein. Rather, these embodiments are provided so that this disclosure will be thorough and complete, and will fully convey the scope of the present disclosure to those skilled in the art. Like numbers refer to like elements throughout, and base 100 reference numerals are used to indicate similar elements in alternative embodiments.

Referring initially to FIG. 1, a patient monitoring system 100 according to the present disclosure is now described. The patient monitoring system 100 is for monitoring a patient 101. The patient monitoring system 100 illustratively comprises a server 102, and a patient monitoring device 103 in communication with the server over a network (e.g. local area network (LAN) or the Internet).

The patient monitoring device 103 illustratively includes a base 104 and a frame 105 extending upwardly therefrom. In the illustrated embodiment, the patient monitoring device 103 has a typical floor weight scale form factor. The patient monitoring device 103 illustratively comprises a pair of handrails 106a-106b carried by the frame 105 to be grasped by the patient 101.

The patient monitoring device 103 illustratively comprises a weight sensor 107 carried by the base 104. For example, the weight sensor 107 may comprise a pressure sensor, such as a piezoelectric sensor device.

The patient monitoring device 103 illustratively comprises a pair of impedance sensors 110a-110b to be attached to the patient 101 while the patient is on the weight sensor 107. The patient monitoring device 103 illustratively comprises a controller 111 coupled to the pair of impedance sensors 110a-110b and the weight sensor 107.

The controller 111 is configured to cooperate with the pair of impedance sensors 110a-110b to sense a lung impedance of the patient 101. In particular, the controller 111 is configured to cause the pair of impedance sensors 110a-110b to pass an electrical signal therebetween to measure an impedance. As will be appreciated, the lung of the patient 101 is normally composed of multiple air sacs (i.e. "alveoli"). Since air has poor conductivity, it is a high impedance material. Of course, if the lung of the patient 101 were to collect liquid, such as water, the sensed impedance value would drop since water is a better conductor of electricity than air in the alveoli and in the space between the chest wall and the outer surface of the lung where it collects in CHF.

The controller 111 is configured to cooperate with the weight sensor 107 to sense a weight of the patient 101 while simultaneously or near simultaneously (i.e. ±20 seconds) sensing the lung impedance. The controller 111 is configured to determine whether the patient 101 is experiencing CHF based upon at least the lung impedance and the weight of the patient.

In this embodiment, each impedance sensor 110a-110b comprises a wired transmitter configured to communicate with the controller 111 via a wiring harness. In some embodiments, each impedance sensor 110a-110b comprises a flexible suction cup housing, and an electrically conductive electrode carried by the flexible suction cup housing. The flexible suction cup housing is configured to attach to the skin of the patient 101 via a suction effect. Helpfully, the flexible suction cup housing permits the impedance sensor 110a-110b to be reused daily. In other embodiments (FIG. 3), each impedance sensor 110a-110b comprises a wireless transmitter.

In the illustrated embodiment, the patient monitoring device 103 includes a pair of electrodes 112a-112b (e.g. electrically conductive plates) respectively carried by the pair of handrails 106a-106b and coupled to the controller 111. The controller may be configured to sense an electrocardiogram (EKG) rhythm of the patient 101, and determine whether the patient is experiencing CHF further based upon the EKG rhythm of the patient. In some embodiments, the EKG rhythm may comprise a simple heart rate measurement.

Also, the patient monitoring device 103 illustratively comprises a pulse oximetry sensor 113 carried by one of the pair of handrails 106a-106b or the frame 105 and coupled to the controller 111. The controller 111 may be configured to sense an oxygen saturation of the patient 101, and determine whether the patient is experiencing CHF further based upon the oxygen saturation of the patient.

The patient monitoring device 103 illustratively comprises a wireless transceiver 114 (e.g. WiFi IEEE 802.11 transceiver), and an antenna 119 thereto. The wireless transceiver 114 is coupled to the controller 111 and configured to transmit the lung impedance of the patient 101, the weight of the patient, the EKG rhythm of the patient, and the oxygen saturation of the patient. In particular, the wireless transceiver 114 is configured to transmit this data of the patient 101 to the server 102.

In some embodiments, the server 102 may comprise a standalone computing device. In other embodiments, the server 102 may comprise assigned computing resources within a cloud computing platform, such as Amazon Web Services, Microsoft Azure, or Google Cloud Computing Platform. The server 102 is configured to generate alert messages when the received data indicates CHF in the patient 101. In some embodiments, the server 102 provides a monitoring interface for healthcare providers to review daily data from the patient 101.

Referring now additionally to FIGS. 4A-4D, diagrams 1000, 1010, 1020, 1030 show exemplary placement of the pair of impedance sensors 110a-110b for sensing of the lung impedance for the lungs 1005a-1005b of the patient 101. The lung impedance illustratively may be between an anterior chest position 1011a-1011b of the patient 101, and a posterior back position 1001a-1001b of the patient. In particular, the anterior chest positions 1011a-1011b are the right and left chest wall at the fifth rib (i.e. medial to the nipple of the patient 101). The posterior back positions 1001a-1001b are the right and left posterior chest wall (i.e. below the lowermost tip of the scapula 1002a-1002b).

The lung impedance illustratively may additionally or alternatively be between a first lateral chest position 1021a of the patient 101, and a second lateral chest position 1021b opposite the first lateral chest position of the patient. More specifically, the first lateral chest position 1021a may comprise a right midaxillary at the sixth intercostal space (i.e. below the armpit at the nipple level), and the second lateral chest position 1021b may comprise a left midaxillary at the sixth intercostal space (i.e. below the armpit at the nipple level).

In the exemplary diagrams 1000, 1010, 1020, 1030, a total of three pairs of positions are shown, and the pair of impedance sensors 110a-110b may be attached to the patient 101 in any one of these position pairs to generate the lung impedance. In some embodiments, the patient monitoring device 103 comprises a plurality of impedance sensor pairs 110a-110b positioned at a subset or all three pairs of positions. In these embodiments, the lung impedance sensed may comprise an average of the impedance values from the subset or all three pairs of positions.

More specifically, the controller 111 may be configured to determine whether the patient 101 is experiencing the CHF based upon the lung impedance being less than an impedance threshold value. In other words, the lung impedance being less than the impedance threshold value indicates a reduction in impedance due to liquid collecting in the lungs 1005a-1005b of the patient 101. When the alveoli of the lungs 1005a-1005b of the patient 101 start to fill up with liquid because of CHF (i.e. due the inability of the heart to contract efficiently as a pump or due to weakening of the muscles of the heart), then the liquid will start to collect in the lungs because of damming of the fluid behind the heart. The liquid with water and electrolytes in it, is then, able to conduct the electrical signal more effectively than when it was filled with air. This in turn would result in decrease in the "impedance" or the "resistance" of the flow of the electric current and this difference could be recorded and quantified.

The controller 111 is configured to determine whether the patient 101 is experiencing the CHF based upon the EKG rhythm of the patient exhibiting a difference from past EKG rhythms of the patient 101. For example, the controller 111 is configured to flag different kinds of arrhythmias (e.g., irregular heart rhythms, such as atrial fibrillation, supraventricular tachycardia (SVT), bradycardia, tachycardia or other lethal rhythms).

The controller 111 may be configured to determine whether the patient is experiencing the CHF based upon the weight of the patient being greater than a weight threshold value. Here, the controller 111 is flagging weight gain due to water retention, and the weight threshold value would be derived based upon historical weight data for the patient 101. For example, if the weight of the patient 101 increases by more than 1.5%, the controller 111 is configured to flag the result.

In some embodiments, the controller 111 is configured to determine whether the patient 101 is experiencing the CHF based upon a BNP value for the patient being greater than a BNP threshold value. In particular, the BNP value of the patient 101 can be calibrated based upon historical results (e.g. multiple controlled tests during prior hospitalization). The BNP value for the patient is provided by a blood test. The blood test may be conducted separately, and the test results may be uploaded to the server 102. The controller 111 may download the test results for use in the CHF detection algorithm.

In some embodiments, the patient monitoring device 103 comprises a temperature sensor (not shown) coupled to the controller 111. The controller 111 is configured to sense a temperature of the patient 101, and determine whether the patient 101 is experiencing the CHF based upon the temperature of the patient.

In yet other embodiments, the patient monitoring device 103 comprises a blood pressure sensor (not shown) coupled to the controller 111. The controller 111 is configured to sense a blood pressure of the patient 101, and determine whether the patient 101 is experiencing the CHF based upon the blood pressure of the patient.

Yet another aspect is directed to a method of making a patient monitoring system 100 for a patient 101. The method includes mounting a weight sensor 107 on a base 104 with a frame 105 extending upwardly therefrom, and mounting a pair of handrails 106a-106b on the frame to be grasped by the patient. The method comprises providing at least one pair of impedance sensors 110a-110b to be attached to the patient 101 while the patient is on the weight sensor 107, and coupling a controller 111 to the at least one pair of impedance sensors and the weight sensor and configured to sense a lung impedance of the patient, sense a weight of the patient, and determine whether the patient is experiencing CHF based upon the lung impedance and the weight of the patient.

Figure 2:
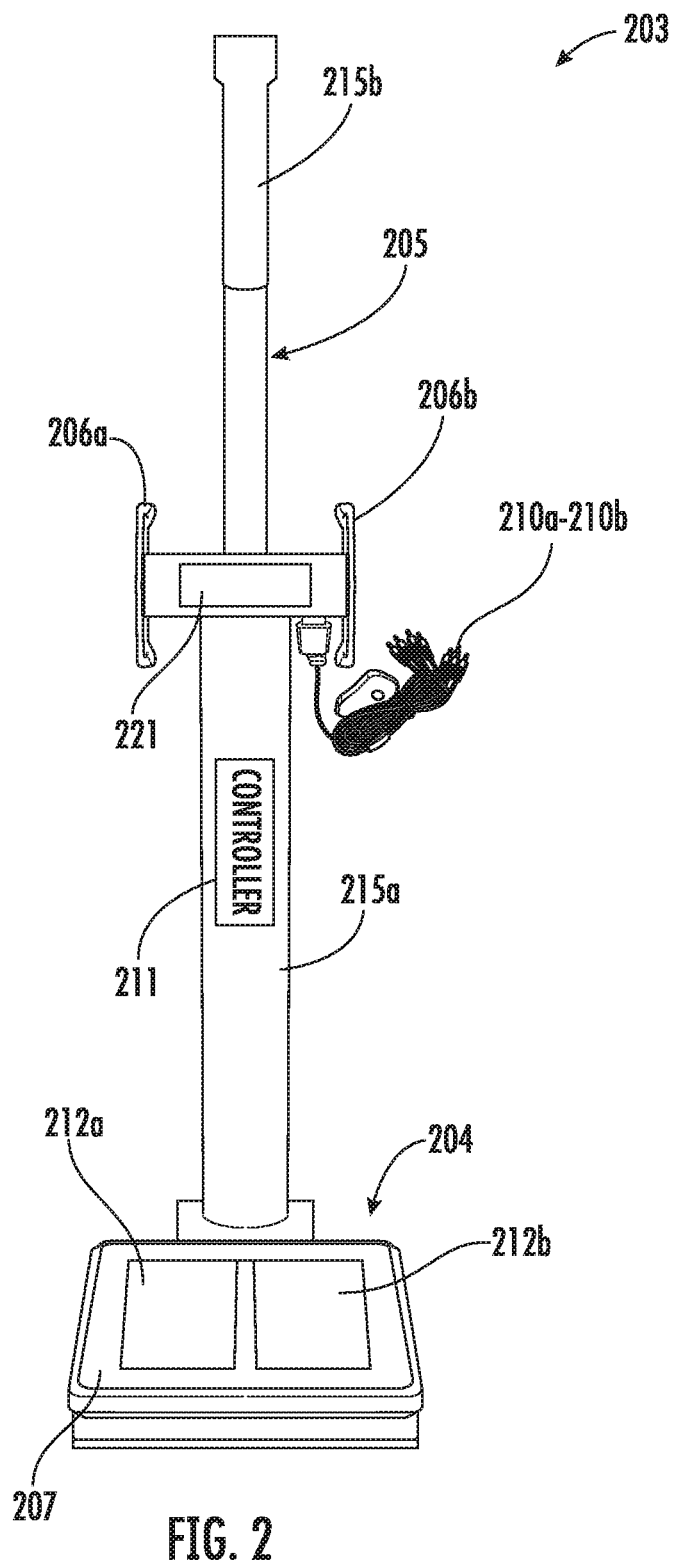
FIG. 2 is a schematic perspective view of a second example embodiment of the patient monitoring system, according to the present disclosure.

Referring now additionally to FIG. 2, another embodiment of the patient monitoring device 203 is now described. In this embodiment of the patient monitoring device 203, those elements already discussed above with respect to FIG. 1 are incremented by 100 and most require no further discussion herein. This embodiment differs from the previous embodiment in that this patient monitoring device 203 illustratively includes the frame 205 comprising a lower frame portion 215a extending from the base 204 and carrying the pair of handrails 206a-206b, and an upper frame portion 215b extending upward from the pair of handrails and defining a linear measuring device for measuring a height of the patient (not shown for illustrative clarity). Also, in this embodiment, the patient monitoring device 203 includes a pair of electrodes 212a-212b respectively carried by the base 204. In some embodiments, the patient monitoring device 203 includes the pair of electrodes 212a-212b respectively carried by the base 204, and an additional pair of electrodes respectively carried by the pair of handrails 206a-206b to provide first and second EKG rhythms of the patient. The patient monitoring device 203 illustratively comprises a display 221 coupled to the controller 211 and configured to provide a user interface for guiding the patient through the process.

In yet other embodiments, the controller 211 is configured to cooperate with both the pair of electrodes 212a-212b and the pair of impedance sensors 210a-210b to generate the EKG rhythm of the patient. In particular, the pair of impedance sensors 210a-210b going across the chest wall would serve as anterior leads. As will be appreciated, in a typical EKG machine, there are the V1, V2, V3, V4, V5 & V6 leads. In this embodiment, the anterior leads on the chest wall monitor the impedance: medial to the nipple, would serve as the V1 and V2 leads. The lead on the left lateral chest wall below the axilla in the fifth or sixth intercostal space would act as the V6 lead.

The right lateral chest wall lead, attached to the lower part of the right armpit at the level of the fifth or sixth intercostal space, can be brought forwards and used as V3 lead. The leads, which was used behind on the back below the tip of the right scapula or shoulder blade, could be brought to the front and used as the V4 lead. Similarly, the lead used behind on the back below the tip of the left scapula or shoulder blade could be brought to the front and used as the V5 lead. This could complete the EKG lead placement.

This is possible by using a combination of the limb leads to form the axial plane by using the pair of electrodes 212a-212b on the base 104 as the contact for the lower limbs and the additional pair of electrodes carried by the pair of handrails 106a-106b on the two sides of the display 221 when grasped by the patient to be used as the upper limb leads contacts and the leads placed across the chest wall as described above to complete the frontal leads.

Figure 3:
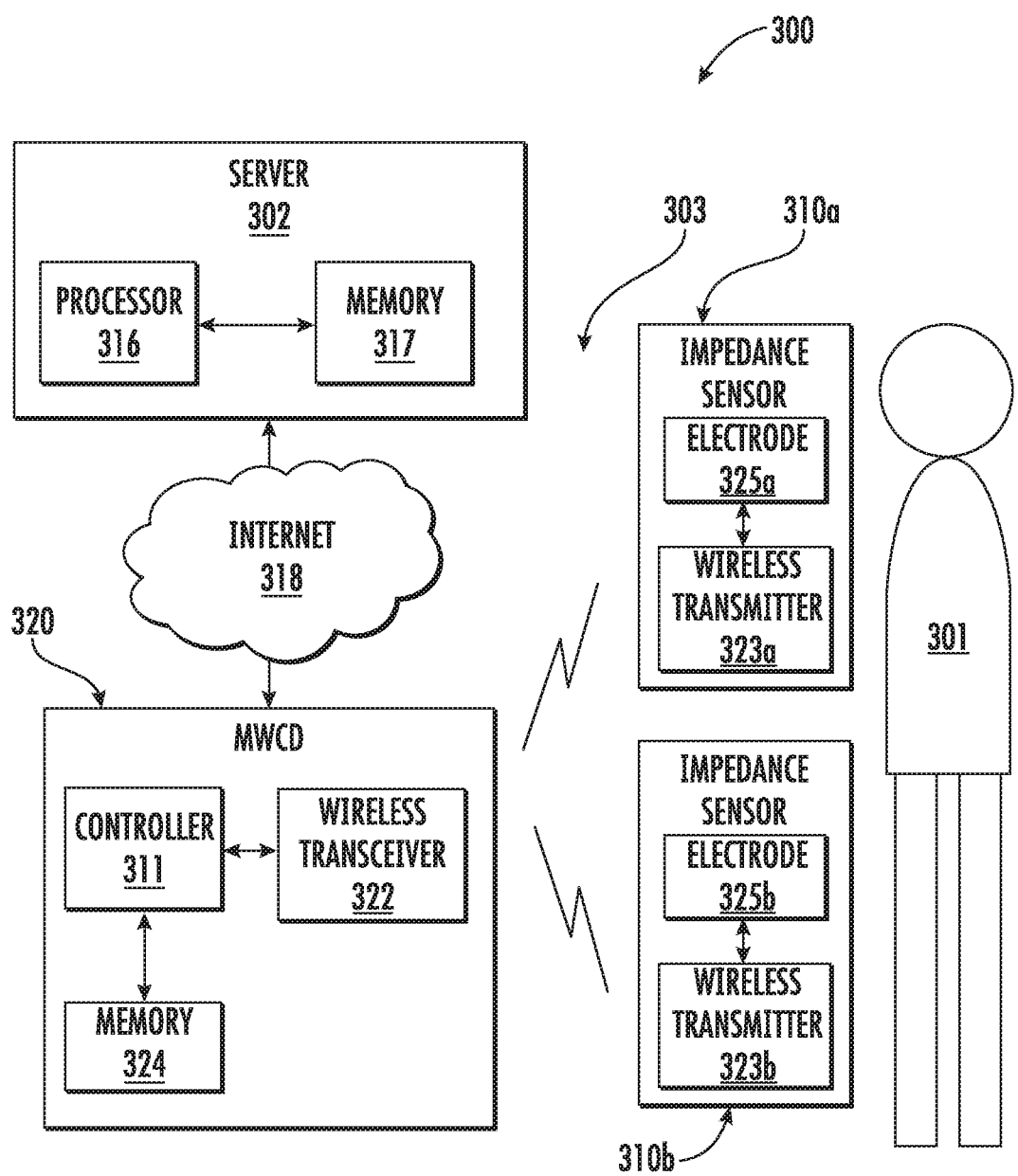
FIG. 3 is a schematic diagram of a third example embodiment of the patient monitoring system, according to the present disclosure.
Figure 4A:
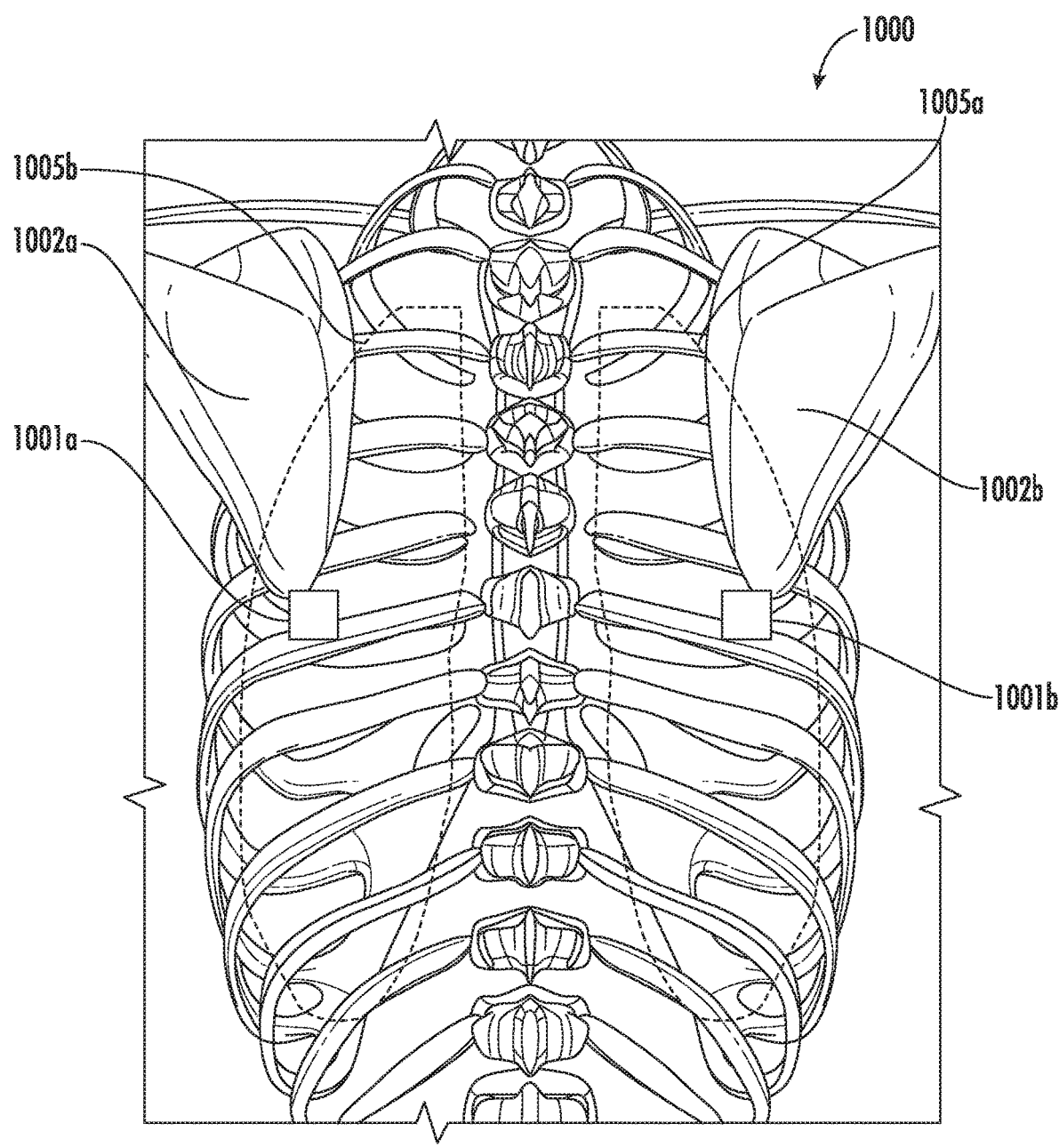
FIGS. 4A-4D are schematic diagrams of placement of impedance sensors on the patient in the patient monitoring system, according to the present disclosure.
Figure 4B:
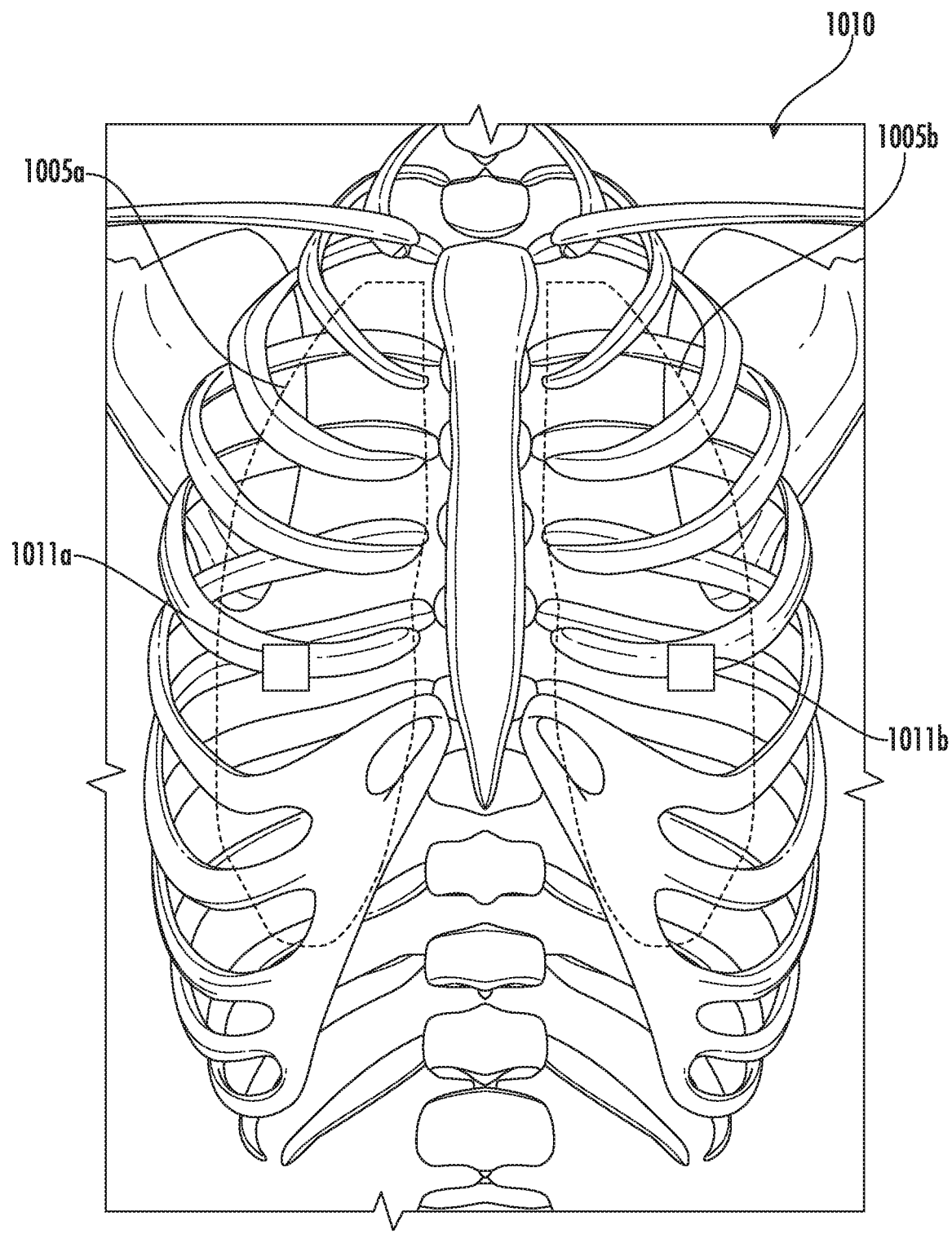
Figure 4C:
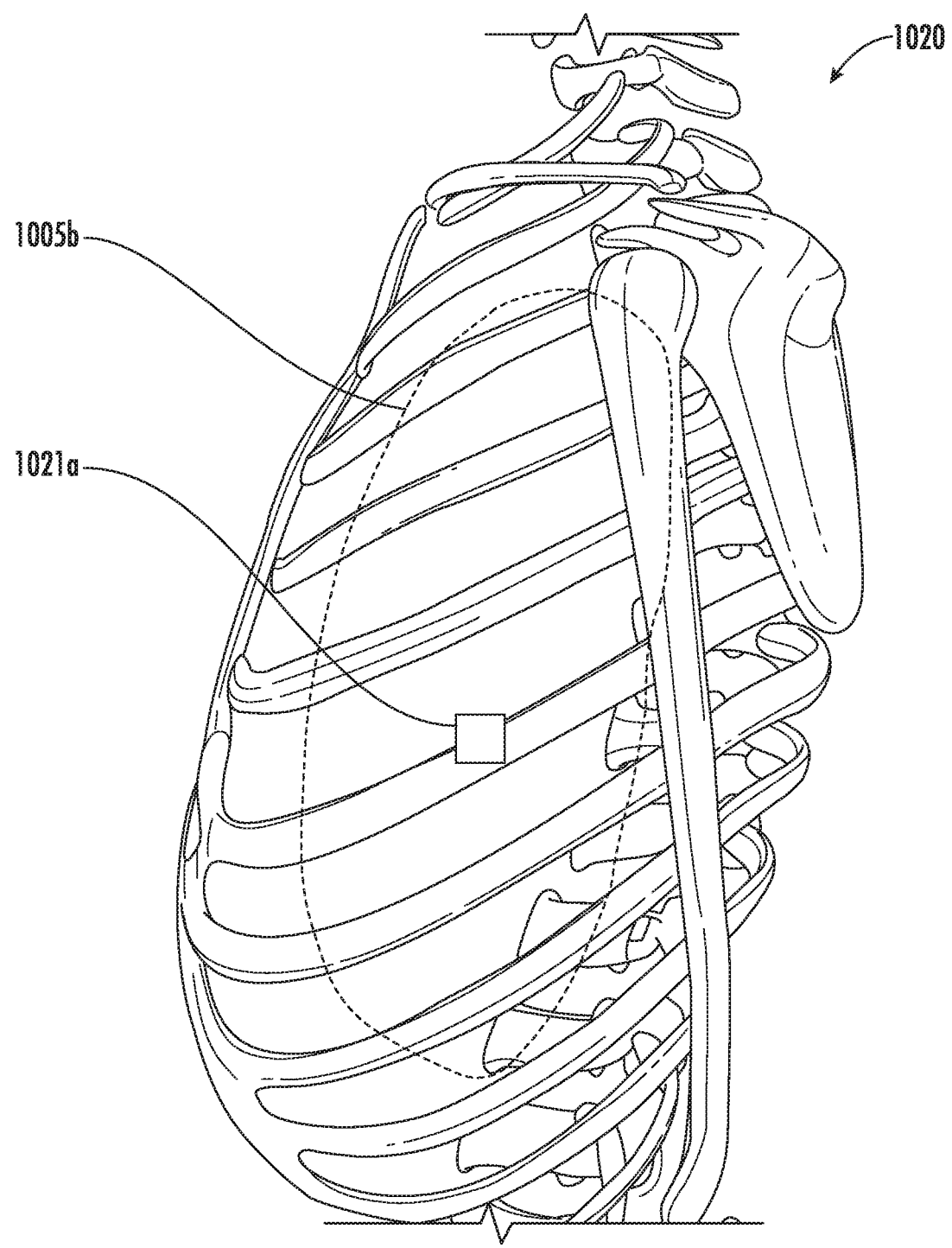
Figure 4D:
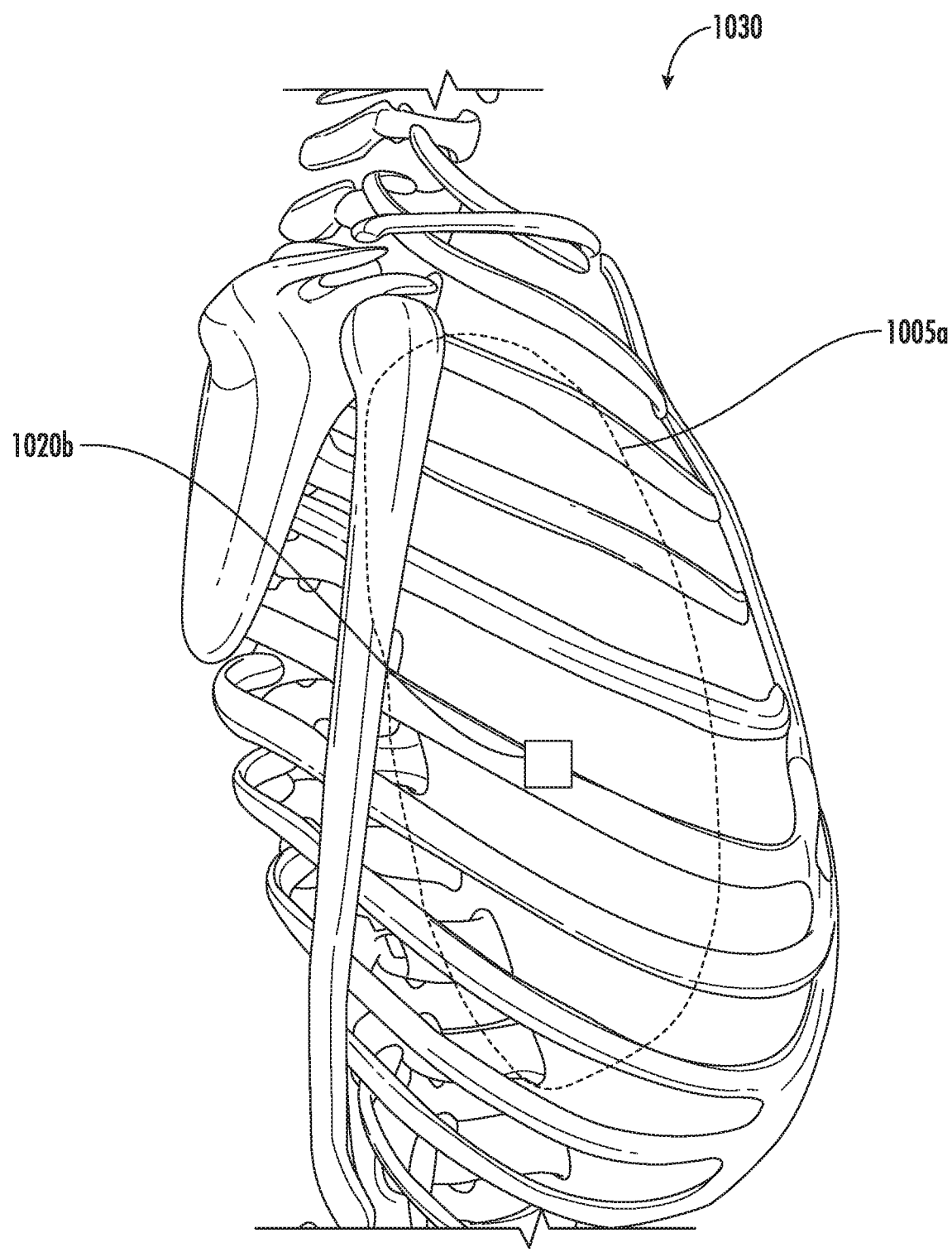

Referring now additionally to FIG. 3, another embodiment of the patient monitoring system 300 is now described. In this embodiment of the patient monitoring system 300, those elements already discussed above with respect to FIG. 1 are incremented by 200 and most require no further discussion herein. This embodiment differs from the previous embodiment in that this patient monitoring system 300 illustratively includes the server 302 comprising a processor 316, and a memory 317 coupled thereto. The server 302 may be geographically remote to the patient monitoring device 303 and illustratively communicates therewith via the Internet 318.

Here, the patient monitoring device 303 illustratively includes a mobile wireless communications device 320 (e.g.

mobile cellular device, tablet computing device, an electronic wrist watch, or a smart watch), and a pair of impedance sensors 310a-310b in communication with the mobile wireless communications device. The mobile wireless communications device 320 illustratively comprises a controller 311, and a wireless transceiver 322 coupled thereto. Each impedance sensor 310a-310b comprises an electrode 325a-325b, a wireless transmitter (or transceiver) 323a-323b coupled to the electrode and configured to communicate with the controller 311 via wireless communications, and a power source (not shown, e.g., battery) coupled to the wireless transmitter. For example, the wireless transceiver 322 and the wireless transmitter 323a-323b may comprise a Bluetooth transceiver or ZigBee transceiver.

The mobile wireless communications device 320 may comprise a memory 324 coupled to the controller 311 and configured to store the sensed data about the patient 301. In some embodiments, the data may be batch transmitted to the server 302. In these embodiments, the transmitted data may be automatically stored within an electronic health record of the patient 301. In yet other embodiments, the patient 301 may provide the mobile wireless communications device 320 to the healthcare provider for review of the data without offboarding the data, thereby enhancing privacy.

Advantageously, the patient monitoring systems 100, 300 and devices 103, 203, 303 may provide an effective approach for monitoring the patient 101, 301 once discharged from the hospital. Particularly, for patients with cardiac issues, the patient monitoring systems 100, 300 and devices 103, 203, 303 may provide a method for the healthcare provider to continuously monitor the patient 101, 301 with little effort from the patient. Indeed, the patient 101, 301 need only operate the patient monitoring device 103, 203, 303 to give the healthcare provider a snapshot of patient cardiac health. If conditions warrant, the patient monitoring devices 103, 203, 303 flag the patient data for manual review by the healthcare provider.

Many modifications and other embodiments of the present disclosure will come to the mind of one skilled in the art having the benefit of the teachings presented in the foregoing descriptions and the associated drawings. Therefore, it is understood that the present disclosure is not to be limited to the specific embodiments disclosed, and that modifications and embodiments are intended to be included within the scope of the appended claims.

That which is claimed is:

1. A patient monitoring system for a patient, the patient monitoring system comprising:
    a base and a frame extending upwardly therefrom;
    a weight sensor carried by said base;
    a pair of handrails carried by said frame to be grasped by the patient;
    at least one pair of impedance sensors to be attached to the patient while the patient is on the weight sensor comprising a first impedance sensor to be positioned on an anterior chest position of the patient, and a second impedance sensor to be positioned on a posterior back position of the patient; and
    a controller coupled to said at least one pair of impedance sensors and said weight sensor and configured to
        sense a lung impedance of the patient based upon the at least one pair of impedance sensors,
        sense a weight of the patient, and
        determine whether the patient is experiencing congestive heart failure (CHF) based upon the lung impedance and the weight of the patient.

2. The patient monitoring system of claim 1 further comprising a pair of electrodes respectively carried by said pair of handrails and coupled to said controller.

3. The patient monitoring system of claim 1 further comprising a pulse oximetry sensor coupled to said controller.

4. The patient monitoring system of claim 1 wherein the at least one pair of impedance sensors comprises a third impedance sensor to be positioned on a first lateral chest position of the patient, and a fourth impedance sensor to be positioned on a second lateral chest position opposite the first lateral chest position of the patient.

5. The patient monitoring system of claim 1 further comprising a wireless transceiver coupled to said controller and configured to transmit the lung impedance of the patient and the weight of the patient to a server.

6. The patient monitoring system of claim 1 wherein said controller is configured to determine whether the patient is experiencing the CHF based upon the lung impedance being less than an impedance threshold value.

7. The patient monitoring system of claim 1 wherein said controller is configured to determine whether the patient is experiencing the CHF based upon the weight of the patient being greater than a weight threshold value.

8. The patient monitoring system of claim 1 wherein said controller is configured to download beta natriuretic peptide (BNP) test result values for the patient and determine whether the patient is experiencing the CHF based upon a downloaded BNP test result value for the patient being greater than a BNP threshold value.

9. The patient monitoring system of claim 1 wherein each impedance sensor comprises an electrode, and a wireless transmitter coupled thereto and configured to communicate with said controller.

10. A patient monitoring system for a patient, the patient monitoring system comprising:
    a server; and
    a patient monitoring device in communication with said server and comprising
        a base and a frame extending upwardly therefrom,
        a weight sensor carried by said base,
        a pair of handrails carried by said frame to be grasped by the patient,
    at least one pair of impedance sensors to be attached to the patient while the patient is on the weight sensor comprising a first impedance sensor to be positioned on an anterior chest position of the patient, and a second impedance sensor to be positioned on a posterior back position of the patient,
        a pair of electrodes respectively carried by said pair of handrails,
        a controller coupled to said at least one pair of impedance sensors, said weight sensor, and said pair of electrodes,
        said controller configured to
            sense a lung impedance of the patient based upon the at least one pair of impedance sensors,
            sense a weight of the patient, and
            determine whether the patient is experiencing congestive heart failure (CHF) based upon the lung impedance, and the weight of the patient, and
        a wireless transceiver coupled to said controller and configured to transmit the lung impedance of the patient, and the weight of the patient to said server.

11. The patient monitoring system of claim 10 wherein said patient monitoring device further comprises a pulse oximetry sensor coupled to said controller.

12. The patient monitoring system of claim 10 wherein the at least one pair of impedance sensors comprises a third impedance sensor to be positioned on a first lateral chest position of the patient, and a fourth impedance sensor to be positioned on a second lateral chest position opposite the first lateral chest position of the patient.

13. The patient monitoring system of claim 10 wherein said controller is configured to determine whether the patient is experiencing the CHF based upon the lung impedance being less than an impedance threshold value.

14. The patient monitoring system of claim 10 wherein said controller is configured to determine whether the patient is experiencing the CHF based upon the weight of the patient being greater than a weight threshold value.

15. The patient monitoring system of claim 10 wherein said controller is configured to download beta natriuretic peptide (BNP) test result values for the patient and determine whether the patient is experiencing the CHF based upon a downloaded BNP test result value for the patient being greater than a BNP threshold value.

16. A method of making a patient monitoring system for a patient, the method comprising:
mounting a weight sensor on a base with a frame extending upwardly therefrom;
mounting a pair of handrails on the frame to be grasped by the patient;
providing at least one pair of impedance sensors to be attached to the patient while the patient is on the weight sensor comprising a first impedance sensor to be positioned on an anterior chest position of the patient, and a second impedance sensor to be positioned on a posterior back position of the patient; and
coupling a controller to the at least one pair of impedance sensors and the weight sensor and configured to
sense a lung impedance of the patient based upon the at least one pair of impedance sensors,
sense a weight of the patient, and
determine whether the patient is experiencing congestive heart failure (CHF) based upon the lung impedance and the weight of the patient.

17. The method of claim 16 further comprising positioning a pair of electrodes respectively carried by the pair of handrails and coupled to the controller.

18. The method of claim 16 further comprising positioning a pulse oximetry sensor coupled to the controller.

19. A patient monitoring system for a patient, the patient monitoring system comprising:
a base and a frame extending upwardly therefrom;
a weight sensor carried by said base;
a pair of handrails carried by said frame to be grasped by the patient;
at least one pair of impedance sensors to be attached to the patient while the patient is on the weight sensor comprising a first impedance sensor to be positioned on a first lateral chest position of the patient, and a second impedance sensor to be positioned on a second lateral chest position opposite the first lateral chest position of the patient; and
a controller coupled to said at least one pair of impedance sensors and said weight sensor and configured to
sense a lung impedance of the patient based upon the at least one pair of impedance sensors,
sense a weight of the patient, and
determine whether the patient is experiencing congestive heart failure (CHF) based upon the lung impedance and the weight of the patient.

20. The patient monitoring system of claim 19 further comprising a pair of electrodes respectively carried by said pair of handrails and coupled to said controller.

21. The patient monitoring system of claim 19 further comprising a pulse oximetry sensor coupled to said controller.

22. The patient monitoring system of claim 19 further comprising a wireless transceiver coupled to said controller and configured to transmit the lung impedance of the patient and the weight of the patient to a server.

23. The patient monitoring system of claim 19 wherein said controller is configured to determine whether the patient is experiencing the CHF based upon the lung impedance being less than an impedance threshold value.

* * * * *